(12) United States Patent
Oka et al.

(10) Patent No.: US 6,306,603 B1
(45) Date of Patent: Oct. 23, 2001

(54) CD36 MUTANT GENE AND METHODS FOR DIAGNOSING DISEASES CAUSED BY ABNORMAL LIPID METABOLISM AND DIAGNOSTIC KITS THEREFOR

(75) Inventors: Takanori Oka; Akio Yamane, both of Takata-Gun; Takao Tanaka, Ibaraki, all of (JP)

(73) Assignee: Wakunaga Phaemaceutical Co., Ltd., Osaka (JP)

(*) Notice: Subject to any disclaimer, the term of this patent is extended or adjusted under 35 U.S.C. 154(b) by 0 days.

(21) Appl. No.: 09/476,124

(22) Filed: Jan. 3, 2000

(30) Foreign Application Priority Data

Jan. 8, 1999 (JP) .................................................. 11-003446
Sep. 17, 1999 (JP) .................................................. 11-264052

(51) Int. Cl.⁷ ............................. C07H 21/04; C12Q 1/68; C12P 19/34
(52) U.S. Cl. ......................... 435/6; 536/24.3; 536/24.33; 536/23.1; 435/91.2; 435/91.1
(58) Field of Search ................................. 536/23.1, 24.1, 536/24.2, 24.33, 25.3, 24.3; 435/91.1, 91.2, 91.5, 6, 810, 501

(56) References Cited

PUBLICATIONS

Taylor et al. Characterization of two alternatively pliced 5'—untranslated exons of the human CD36 gene different cell types. Gene vol. 133, pp. 205–212.*

Armesilla et al. Structural Organization of the Gene for Human CD36 Glycoprotein. The Journal of Biological Chemistry. vol. 269, No. 29, pp. 18985–18991, Jul. 1994.*

Taylor et al. Characterization of two alternatively pliced 5'—untranslated exons of the human CD36 gene different cell types. Gene vol. 133, pp. 205–212, Nov. 1993.*

Angel L. Armesilla, et al., *The Journal of Bilogical Chemistry*, vol. 269, No. 29, Issue of Jul. 22, pp. 18985–18991 (1994).

Takao Tanaka, et al., *J. Mol Cell Cardiol*, vol. 29, pp. 121–127 (1997).

* cited by examiner

*Primary Examiner*—Stephanie W. Zitomer
*Assistant Examiner*—Cynthia B Wilder
(74) *Attorney, Agent, or Firm*—Oblon, Spivak, McClelland, Maier & Neustadt, P.C.

(57) ABSTRACT

The present invention provides CD36 mutant gene and methods and kits for diagnosing diseases caused by a lipid metabolism abnormality.

14 Claims, No Drawings

SEQUENCE LISTING

<160> NUMBER OF SEQ ID NOS: 44

<210> SEQ ID NO 1
<211> LENGTH: 112
<212> TYPE: DNA
<213> ORGANISM: Homo sapiens

<400> SEQUENCE: 1
agtttatatg ttcataatta ttttcaacgt atattacaga gtattaaaga atctgaagag     60
gaactatctt tggcttaatg aggtttgtat ttgcagctgt tagtcattaa aa             112

<210> SEQ ID NO 2
<211> LENGTH: 167
<212> TYPE: DNA
<213> ORGANISM: Homo sapiens

<400> SEQUENCE: 2
agtttatatg ttcataatta ttttcaacgt atattacaga gtattaaaga atctgaagag     60
gaactatatt gtgcctattc tttggcttaa agaatctgaa gaggaactat attgtgccta   120
ttctttggct taatgaggtt tgtatttgca gctgttagtc attaaaa                 167

<210> SEQ ID NO 3
<211> LENGTH: 114
<212> TYPE: DNA
<213> ORGANISM: Homo sapiens

<400> SEQUENCE: 3
agtttatatg ttcataatta ttttcaacgt atattaaaga atctgaagag gaactatatt    60
gtgcctattc tttggcttaa tgaggtttgt atttgcagct gttagtcatt aaaa          114

<210> SEQ ID NO 4
<211> LENGTH: 127
<212> TYPE: DNA
<213> ORGANISM: Homo sapiens

<400> SEQUENCE: 4
ttggtaatta tttagttgtt ctcttaactg gattcacttt acaatttgca aaacggctgc    60
aggtcaacct attggtcaag ccatcagaaa aaattcagtg agtctcttga aatggttat   120 tttgata                                                              127

<210> SEQ ID NO 5
<211> LENGTH: 130
<212> TYPE: DNA
<213> ORGANISM: Homo sapiens

<400> SEQUENCE: 5
ctaatcattt gccactcgat ttttaaacag atgcagcctc acttccacct tttgttgaga    60
aaagccaggt attgcagttc ttttcttctg atatttgcag gtaagacaga tactgaagta   120
taagtatgct                                                           130

<210> SEQ ID NO 6
<211> LENGTH: 241
<212> TYPE: DNA
<213> ORGANISM: Homo sapiens

<400> SEQUENCE: 6
ttgtcttaaa cagtgacttt gtttttgtag gctgcatccc atatctatca aaatcaattt    60

```
gttcaaatga tcctcaattc acttattaac aagtcaaaat cttctatgtt ccaagtcaga        120
actttgagag aactgttatg gggctatagg gatccatttt ttgagtttgg ttccgtaccc        180
tgttactacc acagttggtc tgttttatcc tgtaagtacc aaatatgaat ggcaatatta       240
t                                                                        241

<210> SEQ ID NO 7
<211> LENGTH: 240
<212> TYPE: DNA
<213> ORGANISM: Homo sapiens

<400> SEQUENCE: 7
ttgtcttaaa cagtgacttt gttttgtag gctgcatccc atatctatca aaatcaattt         60
gttcaaatga tcctcaattc acttattaac aagtcaaaat cttctaggtt ccaagtcaga       120
actttgagag aactgttatg gggctatagg gatccatttt tgagtttggt tccgtaccct       180
gttactacca cagttggtct gttttatcct gtaagtacca aatatgaatg caatattat        240

<210> SEQ ID NO 8
<211> LENGTH: 207
<212> TYPE: DNA
<213> ORGANISM: Homo sapiens

<400> SEQUENCE: 8
tttgaatttt gtttactgct gtttctttag agttcgtttt ctagccaagg aaaatgtaac        60
ccaggacgct gaggacaaca cagtctcttt cctgcagccc aatggtgcca tcttcgaacc       120
ttcactatca gttggaacag aggctgcaac ttcacagctc tcaatctggc tgtggcagtg      180
agtagacaaa caacaaagtt atctatt                                            207

<210> SEQ ID NO 9
<211> LENGTH: 1870
<212> TYPE: DNA
<213> ORGANISM: Homo sapiens

<400> SEQUENCE: 9 gaaaatcct tcttagccat tttaaagata gctttccaat gattagacga attgattctt         60
tctgtgactc atcagttcct ttcctgtaaa attcatgtct tgctgttgat ttgtgaataa       120
gaaccagagc ttgtagaaac cactttaatc atatccagga gtttgcaaga aacaggtgct       180
taacactaat tcacctcctg aacaagaaaa atgggctgtg accggaactg tgggctcatc      240 gctgggctg tcattggtgc tgtcctggct gtgtttggag gtattctaat gccagttgga        300
gacctgctta tccagaagac aattaaaaag caagttgtcc tcgaagaagg tacaattgct       360
tttaaaaatt gggttaaaac aggcacagaa gtttacagac agttttggat ctttgatgtg       420
caaaatccac aggaagtgat gatgaacagc agcaacattc aagttaagca agaggtcct        480 tatacgtaca gagttcgttt tctagccaag gaaaatgtaa cccaggacgc tgaggacaac       540
acagtctctt tcctgcagcc caatggtgcc atcttcgaac cttcactatc agttggaaca       600 gaggctgcaca acttcacagt tctcaatctg gctgtggcag ctgcatccca tatctatcaa      660 aatcaattg ttcaaatgat cctcaattca cttattaaca agtcaaaatc ttctatgttc       720
caagtcagaa ctttgagaga actgttatgg ggctatagg atccattttt gagtttggtt       780
ccgtaccctg ttactaccac agttggtctg ttttatcctt acaacaatac tgcagatgga      840
gtttataaag ttttcaatgg aaaagataac ataagtaaag ttgccataat cgacacatat      900
```

```
aaaggtaaaa ggaatctgtc ctattgggaa agtcactgcg acatgattaa tggtacagat      960
gcagcctcat ttccacctttt tgttgagaaa agccaggtat tgcagttctt ttcttctgat    1020
atttgcaggt caatctatgc tgtatttgaa tccgacgtta atctgaaagg aatccctgtg     1080
tatagatttg ttcttccatc caaggccttt gcctctccag ttgaaaaccc agacaactat    1140
tgtttctgca cagaaaaaat tatctcaaaa aattgtacat catatggtgt gctagacatc    1200
agcaaatgca agaagggag acctgtgtac atttcacttc ctcatttct gtatgcaagt      1260 cctgatgttt cagaacctat tgatggatta acccaaatg aagaagaaca taggacatac     1320
ttggatattg aacctataac tggattcact ttacaatttg caaaacggct gcaggtcaac    1380
ctattggtca agccatcaga aaaaattcaa gtattaaaga atctgaagag gaactatatt    1440
gtgcctattc tttggcttaa tgagactggg accattggtg atgagaaggc aaacatgttc    1500
agaagtcaag taactggaaa aataaacctc cttggcctga tagaaatgat cttactcagt    1560
gttggtgtgg tgatgtttgt tgcttttatg atttcatatt gtgcatgcag atcgaaaaca    1620
ataaaataag tatgtaccaa aaaatattgc ttcaataata ttagcttata tattacttgt    1680 tttcactttta tcaaagagaa gttacatatt aggccatata tatttctaga catgtctagc   1740
cactgatcat ttttaaatat aggtaaataa acctataaat attatcacgc agatcactaa    1800
agtatatctt taattctggg agaaatgaga taaaagatgt acttgtgacc attgtaacaa    1860
tagcacaaat                                                          1870

<210> SEQ ID NO 10
<211> LENGTH: 221
<212> TYPE: DNA
<213> ORGANISM: Homo sapiens

<400> SEQUENCE: 10
cataacccaa acttattttc ttttccatag caagttgtcc tcgaagaagg tacaattgct      60
tttaaaaatt gggttaaaac aggcacagaa gtttacagac agttttggat ctttgatgtg     120
caaaatccac aggaagtgat gatgaacagc agcaacattc aagttaagca aagaggttct    180
tatacgtaca ggtgagtgag tgcccacaaa tatgagacac t                        221

<210> SEQ ID NO 11
<211> LENGTH: 206
<212> TYPE: DNA
<213> ORGANISM: Homo sapiens

<400> SEQUENCE: 11
tttgaatttt gtttactgct gtttctttag agttcgtttt ctagccaagg aaaatgtaac      60
ccaggacgct gaggacaaca gtctctttcc tgcagcccaa tggtgccatc ttcgaacctt    120
cactatcagt tggaacagag gctgacaact tcacagttct caatctggct gtggcagtga    180
gtagacaaac aacaaagtta tctatt                                         206

<210> SEQ ID NO 12
<211> LENGTH: 251
<212> TYPE: DNA
<213> ORGANISM: Homo sapiens

<400> SEQUENCE: 12
tggaatgcag ctcttttttc tctgtattta ggtcaatcta tgctgtatttt gaatccgacg     60 ttaatctgaa aggaatccct gtgtatagat ttgttcttcc atccaaggcc tttgcctctc    120
cagttgaaaa cccagacaac tattgtttct gcacagaaaa aattatctca aaaaaattgt    180
```

-continued

```
acatcatatg gtgtgctaga catcagcaaa tgcaaagaag gtgagtaaat aacctcagta      240
gcacagtcca t                                                          251

<210> SEQ ID NO 13
<211> LENGTH: 25
<212> TYPE: DNA
<213> ORGANISM: Homo sapiens

<400> SEQUENCE: 13
ttctgtttta tgatctcttt ctaat                                            25

<210> SEQ ID NO 14
<211> LENGTH: 24
<212> TYPE: DNA
<213> ORGANISM: Homo sapiens

<400> SEQUENCE: 14
aatgagagga tattctttga ctac                                             24

<210> SEQ ID NO 15
<211> LENGTH: 26
<212> TYPE: DNA
<213> ORGANISM: Homo sapiens

<400> SEQUENCE: 15
cataacccaa acttattttc ttttcc                                           26

<210> SEQ ID NO 16
<211> LENGTH: 25
<212> TYPE: DNA
<213> ORGANISM: Homo sapiens

<400> SEQUENCE: 16
agtgtctcat atttgtgggc actca                                            25

<210> SEQ ID NO 17
<211> LENGTH: 25
<212> TYPE: DNA
<213> ORGANISM: Homo sapiens

<400> SEQUENCE: 17
tttgaatttt gtttactgct gtttc                                            25

<210> SEQ ID NO 18
<211> LENGTH: 26
<212> TYPE: DNA
<213> ORGANISM: Homo sapiens

<400> SEQUENCE: 18
aatagataac tttgttgttt gtctac                                           26

<210> SEQ ID NO 19
<211> LENGTH: 25
<212> TYPE: DNA
<213> ORGANISM: Homo sapiens

<400> SEQUENCE: 19
ttgtcttaaa cagtgacttt gtttt                                            25

<210> SEQ ID NO 20
<211> LENGTH: 25
<212> TYPE: DNA
```

```
<213> ORGANISM: Homo sapiens

<400> SEQUENCE: 20
ataatattgc cattcatatt tggta                                  25

<210> SEQ ID NO 21
<211> LENGTH: 25
<212> TYPE: DNA
<213> ORGANISM: Homo sapiens

<400> SEQUENCE: 21
aagtaacatt ttcccataca tatat                                  25

<210> SEQ ID NO 22
<211> LENGTH: 25
<212> TYPE: DNA
<213> ORGANISM: Homo sapiens

<400> SEQUENCE: 22
catacatgca cattttacca gaata                                  25

<210> SEQ ID NO 23
<211> LENGTH: 25
<212> TYPE: DNA
<213> ORGANISM: Homo sapiens

<400> SEQUENCE: 23
tgtttattca ttgtcttttt ctatt                                  25

<210> SEQ ID NO 24
<211> LENGTH: 25
<212> TYPE: DNA
<213> ORGANISM: Homo sapiens

<400> SEQUENCE: 24
ctgtgatgac cacaaaacaa atatt                                  25

<210> SEQ ID NO 25
<211> LENGTH: 25
<212> TYPE: DNA
<213> ORGANISM: Homo sapiens

<400> SEQUENCE: 25
ctaatcattt gccactcgat tttta                                  25

<210> SEQ ID NO 26
<211> LENGTH: 25
<212> TYPE: DNA
<213> ORGANISM: Homo sapiens

<400> SEQUENCE: 26
agcatactta tacttcagta tctgt                                  25

<210> SEQ ID NO 27
<211> LENGTH: 25
<212> TYPE: DNA
<213> ORGANISM: Homo sapiens

<400> SEQUENCE: 27
tggaatgcag ctcttttttc tctgt                                  25

<210> SEQ ID NO 28
<211> LENGTH: 25
```

```
<212> TYPE: DNA
<213> ORGANISM: Homo sapiens

<400> SEQUENCE: 28
atggactgtg ctactgaggt tattt                                    25

<210> SEQ ID NO 29
<211> LENGTH: 25
<212> TYPE: DNA
<213> ORGANISM: Homo sapiens

<400> SEQUENCE: 29
ttccaattga ctcttaaaac ttgtc                                    25

<210> SEQ ID NO 30
<211> LENGTH: 25
<212> TYPE: DNA
<213> ORGANISM: Homo sapiens

<400> SEQUENCE: 30
ccaaatcaga tcaataaggt gtttt                                    25

<210> SEQ ID NO 31
<211> LENGTH: 25
<212> TYPE: DNA
<213> ORGANISM: Homo sapiens

<400> SEQUENCE: 31
ttggtaatta tttagttgtt ctctt                                    25

<210> SEQ ID NO 32
<211> LENGTH: 30
<212> TYPE: DNA
<213> ORGANISM: Homo sapiens

<400> SEQUENCE: 32
ttggtaatta tttagttgtt ctcttttag                                30

<210> SEQ ID NO 33
<211> LENGTH: 30
<212> TYPE: DNA
<213> ORGANISM: Homo sapiens

<400> SEQUENCE: 33
tatcaaaata accattttca agagactcac                               30

<210> SEQ ID NO 34
<211> LENGTH: 30
<212> TYPE: DNA
<213> ORGANISM: Homo sapiens

<400> SEQUENCE: 34
agtttatatg ttcataatta ttttcaacgt                               30

<210> SEQ ID NO 35
<211> LENGTH: 30
<212> TYPE: DNA
<213> ORGANISM: Homo sapiens

<400> SEQUENCE: 35
ttttaatgac taacagctgc aaatacaaac                               30

<210> SEQ ID NO 36
```

```
<211> LENGTH: 25
<212> TYPE: DNA
<213> ORGANISM: Homo sapiens

<400> SEQUENCE: 36
aaataatgtt gattattaac ttgat                                           25

<210> SEQ ID NO 37
<211> LENGTH: 25
<212> TYPE: DNA
<213> ORGANISM: Homo sapiens

<400> SEQUENCE: 37
tgaagcaata tttttggta catac                                            25

<210> SEQ ID NO 38
<211> LENGTH: 124
<212> TYPE: DNA
<213> ORGANISM: Homo sapiens

<400> SEQUENCE: 38
agtttatatg ttcataatta ttttcaacgt atattacaga gtattaaaga atctgaagag     60
gaactatatt gtgcctattc tttggcttaa tgaggtttgt atttgcagct gttagtcatt    120
aaaa                                                                 124

<210> SEQ ID NO 39
<211> LENGTH: 134
<212> TYPE: DNA
<213> ORGANISM: Homo sapiens

<400> SEQUENCE: 39
ttggtaatta tttagttgtt ctcttttag ataactggat tcactttaca atttgcaaaa     60
cggctgcagg tcaacctatt ggtcaagcca tcagaaaaaa ttcagtgagt ctcttgaaaa    120
tggttatttt gata                                                      134

<210> SEQ ID NO 40
<211> LENGTH: 250
<212> TYPE: DNA
<213> ORGANISM: Homo sapiens

<400> SEQUENCE: 40
tggaatgcag ctcttttttc tctgtattta ggtcaatcta tgctgtattt gaatccgacg     60
ttaatctgaa aggaatccct gtgtatagat ttgttcttcc atccaaggcc tttgcctctc    120
cagttgaaaa cccagacaac tattgttcct gcacagaaaa aattatctca aaaaattgta    180
catcatatgg tgtgctagac atcagcaaat gcaagaagg tgagtaaata acctcagtag    240
cacagtccat                                                           250

<210> SEQ ID NO 41
<211> LENGTH: 130
<212> TYPE: DNA
<213> ORGANISM: Homo sapiens

<400> SEQUENCE: 41
ctaatcattt gccactcgat ttttaaacag atgcagcctc atttccacct tttgttgaga     60
aaagccaggt attgcagttc ttttcttctg atatttgcag gtaagacaga tactgaagta    120
taagtatgct                                                           130
```

-continued

<210> SEQ ID NO 42
<211> LENGTH: 240
<212> TYPE: DNA
<213> ORGANISM: Homo sapiens

<400> SEQUENCE: 42

```
ttgtcttaaa cagtgacttt gtttttgtag gctgcatccc atatctatca aaatcaatttt    60 gttcaaatga tcctcaattc acttattaac aagtcaaaat cttctatgtt ccaagtcaga   120
actttgagag aactgttatg gggctatagg gatccatttt tgagtttggt tccgtaccct   180
gttactacca cagttggtct gttttatcct gtaagtacca aatatgaatg gcaatattat   240
```

<210> SEQ ID NO 43
<211> LENGTH: 208
<212> TYPE: DNA
<213> ORGANISM: Homo sapiens

<400> SEQUENCE: 43

```
tttgaatttt gtttactgct gtttctttag agttcgtttt ctagccaagg aaaatgtaac    60
ccaggacgct gaggacaaca cagtctcttt cctgcagccc aatggtgcca tcttcgaacc   120
ttcactatca gttggaacag aggctgacaa cttcacagtt ctcaatctgg ctgtggcagt   180
gagtagacaa acaacaaagt tatctatt                                      208
```

<210> SEQ ID NO 44
<211> LENGTH: 221
<212> TYPE: DNA
<213> ORGANISM: Homo sapiens

<400> SEQUENCE: 44

```
cataacccaa acttattttc ttttccatag caagttgtcc tcgaagaagg tacaattgct    60
tttaaaaatt gggttaaaac aggcacagaa gtttacagac agttttggat ctttgatgtg   120
caaaatccac aggaagtgat gatgaacagc agcaacattc aagttaagca aagaggtcct   180
tatacgtaca ggtgagtgag tgcccacaaa tatgagacac t                       221
```

CD36 MUTANT GENE AND METHODS FOR DIAGNOSING DISEASES CAUSED BY ABNORMAL LIPID METABOLISM AND DIAGNOSTIC KITS THEREFOR

BACKGROUND OF THE INVENTION

1. Field of the Invention

The present invention relates to a CD36 mutant gene and its use, more specifically, a method for diagnosing diseases caused by lipid metabolism abnormality using the CD36 mutant gene.

2. Background Art

The development in the search technology in heart nuclear medicine in recent years has made it possible to clinically study myocardial lipid metabolism and discuss abnormalities in the myocardial lipid metabolism in heart diseases. In particular, a number of cases of abnormal fatty acid accumulation on the myocardium in hypertrophic cardiomyopathy have been reported. However, its mechanism has not been revealed.

The heart, which is a driving device for blood circulation in the body, requires a great amount of energy even in normal state, and the energy requirement further increases during exercise and under stress. The major source of energy supply in the myocardium is long chain fatty acids and 70 to 80% of myocardial energy are deemed to be derived from long chain fatty acids. Accordingly, disorders in long chain fatty acid metabolism in the myocardium are considered to result in serious consequence. In fact, it is known that cardiac diseases including sudden death are caused by disorders in the final stage of the long chain fatty acid metabolism, namely, the incorporation system of long chain fatty acids into mitochondria (carnitine shuttle), or abnormalities in enzymes which belong to β oxidation system.

Various theories were suggested for the mechanism of the incorporation of long chain fatty acids into cells, but none of them were confirmed. Recently, we identified a gene which associates with the mechanism of the incorporation of myocardial long chain fatty acids and reported that the responsible product is a glycoprotein CD36 which is usually expressed in the platelet membrane (BIO Clinica, 12 (14), 86–90 (1997)).

CD36 mutant genes so far reported include C478T substitution gene in which cytosine at position 478 of the CD36 gene (exon 4) is substituted by thymine (F. K. Schattauer Verlagsgesellschaft mbH (Stuttgart), 69(5), 481–484 (1993)), 539AC deletion gene in which adenine and thymine at positions 539 and 540 of the CD36 gene (exon 5) are deleted (Blood, 83(12), 3545–3552 (1994)), and 1159A insertion gene in which adenine is inserted at position 1159 of the CD36 gene (exon 10) (Arteriosclerosis, Thrombosis, and Vascular Biology, 16(8), 1026–1032).

However, neither relationship between these CD36 mutant genes and diseases caused by lipid metabolism abnormality nor the presence of CD36 mutant genes other than the above have not been confirmed.

SUMMARY OF THE INVENTION

The present inventors studied expression of CD36 protein in platelets and monocytes in 41 test samples deficient in fatty acid incorporation among test samples selectively taken from subjects who have history of cardiac diseases or might have possibilities of having cardiac diseases, using flow cytometry. The results obtained revealed that neither the platelet nor the monocyte expressed the CD36 protein in all test samples.

Further, the present inventors prepared the chromosomal DNA from the 41 test samples and analyzed gene mutations for the entire exon region. The present inventors also prepared the chromosomal DNA from tissues removed using the Batista operation (an operation to excise a part of the myocardium lacking contractility) on 27 cardiomyopathy patients suffering severe cardiac insufficiency and tried to detect CD36 gene mutations. As a result, the present inventors found new mutations in exon 6, exon 9, exon 12 and exon 13 in addition to known mutations in exon 4, exon 5 and exon 10. Moreover, the present inventors specified an additional new mutation present in exon 5, as well as mutations present in exon 6, exon 9 and exon 13.

An object of the present invention is to provide a CD36 mutant gene and a judgment method and a diagnostic kit for diseases caused by abnormal lipid metabolism.

The present invention provides a CD36 mutant gene which comprises a nucleotide sequence selected from the sequences of SEQ ID NO: 1 through NO: 8.

The present invention also provides a nucleotide fragment which comprises a nucleotide sequence selected from the sequences of SEQ ID NO: 1 through NO: 8, or a mutated portion thereof.

The present invention provides a method of judging diseases caused by abnormal lipid metabolism, which comprises the step of detecting a mutation of the CD36 gene.

The present invention provides a kit for diagnosing diseases caused by lipid metabolism abnormality which comprises a reagent for detecting a mutation of the CD36 gene.

DETAILED DESCRIPTION OF THE INVENTION

The term "mutation" as used herein refers to deletions, substitutions and insertions.

The term "gene mutation" as used herein refers to a mutation existing in one allele as well as a mutation existing in both alleles.

The expression "insertion at base No. X" as used herein means that a base is inserted between base No. X-1 and base No. X.

The expression "base No. of the CD36 gene" as used herein means base No. of the CD36 cDNA sequence, i.e., the nucleotide sequence of SEQ ID NO: 9.

The CD 36 mutant genes according to the present invention comprise nucleotide fragments shown in SEQ ID NO: 1 through NO: 8.

Examples of the CD36 mutant genes according to the present invention include:

a CD36 gene sequence in which the nucleotide sequence portion of SEQ ID NO: 38 (including the sequence encoding exon 13 and its adjacent intron portion) is the nucleotide sequence of SEQ ID NO: 1, 2 or 3;

a CD36 gene sequence in which the nucleotide sequence portion of SEQ ID NO: 39 (including the sequence encoding exon 12 and its adjacent intron portion) is the nucleotide sequence of SEQ ID NO: 4;

a CD36 gene sequence in which the nucleotide sequence portion of SEQ ID NO: 41 (including the sequence encoding exon 9 and its adjacent intron portion) is the nucleotide sequence of SEQ ID NO: 5;

a CD36 gene sequence in which the nucleotide sequence portion of SEQ ID NO: 42 (including the sequence encoding exon 6 and its adjacent intron portion) is the nucleotide sequence of SEQ ID NO: 6 or 7;

a CD36 gene sequence in which the nucleotide sequence of SEQ ID NO: 43 (including the sequence encoding exon 5 and its adjacent intron portion) is the nucleotide sequence portion of SEQ ID NO: 8.

In the present invention, a mutated portion of either one of the nucleotide sequences of SEQ ID NO: 1 through NO: 8 and NO: 10 through NO: 12 comprises a nucleotide sequence of at least 12 (for example, 12 to 40) consecutive nucleotides, preferably at least 20 (for example, 20 to 40) consecutive nucleotides including portions having substitutions, deletions or insertions.

The term "CD36" gene, refers to the CD36 gene disclosed in J. Biol. Chem., Vol. 269, No. 29, 18985–18991 (1994). The term "CD36 mutant gene" refers to a CD36 gene having mutations.

The cDNA sequence of the CD36 gene is depicted in SEQ ID NO: 9. Locations of exons in the nucleotide sequence of SEQ ID NO: 9 areas follows: Exon 1: 1–27, exon2: 28–121, exon3: 122–330, exon4: 331–491, exon5: 492–639, exon6: 640–819, exon7: 820–911, exon 8: 912–958, exon 9: 959–1028, exon 10: 1029–1216, exon 11: 1217–1335, exon 12: 1336–1409, exon 13: 1410–1464, and exon 14: 1465 to the region containing the termination codon.

The known mutated portions of the CD36 mutant gene mentioned in "Background Technology" are shown in SEQ ID NOS: 10, 11 and 12.

Nucleotide sequences containing sequences coding for exon 13, exon 12, exon 10, exon 9, exon 6, exon 5 and exon 4 of the normal CD36 gene are depicted in SEQ ID NOS: 38, 39, 40, 41, 42, 43 and 44, respectively.

CD36 mutant genes and their mutated portions are useful for the detection of mutations of the CD36 gene, and further for the diagnosis and judgement of diseases caused by abnormal lipid metabolism.

The term "mutation of the CD36 gene" as used herein can refer to mutations in regions including exon 4, exon 5, exon 6, exon 9, exon 10, exon 12 and exon 13. The expression "mutation of the CD36 gene" means deletions, substitutions and insertions within these exons, and deletions and substitutions in regions given in an exon through an intron or an intron through an exon, as well as deletions, substitutions and insertions in the 5' control regions and 3' control regions within introns. The term "mutation of the CD36 gene" can be mutations resulting in frameshift or a deletion, substitution or insertion of amino acids.

An example of the mutation within exon 5 is mutation (1): a substitution, deletion or insertion of a base at base No. 620 of the CD36 gene. Preferably, the mutation is a substitution at base No. 620 (thymine) of the CD36 gene by cytosine (see below). Normal CD36 gene sequence (SEQ ID NO: 43): ex05; mutant gene sequence (SEQ ID NO: 8): t620c. Exon 5 is shown with an underline.

```
ex05   TTTGAATTTTGTTTACTGCTGTTTCTTTAGAGTTCGTTTTCTAGCCAAGGAAAATGTAAC  60
t620c  TTTGAATTTTGTTTACTGCTGTTTCTTTAGAGTTCGTTTTCTAGCCAAGGAAAATGTAAC  60
       ************************************************************ ex05   CCAGGACGCTGAGGACAACACAGTCTCTTTCCTGCAGCCCAATGGTGCCATCTTCGAACC  120
t620c  CCAGGACGCTGAGGACAACACAGTCTCTTTCCTGCAGCCCAATGGTGCCATCTTCGAACC  120
       ************************************************************ ex05   TTCACTATCAGTTGGAACAGAGGCTGACAACTTCACAGTTCTCAATCTGGCTGTGGCAGT  180
t620c  TTCACTATCAGTTGGAACAGAGGCTGACAACTTCACAGCTCTCAATCTGGCTGTGGCAGT  180
       ************************************  ****************** ex05   GAGTAGACAAACAACAAAGTTATCTATT                                 208
t620c  GAGTAGACAAACAACAAAGTTATCTATT                                 208
```

Examples of the mutation within exon 6 include mutation (2): a substitution, deletion or insertion at base No. 716 of the CD36 gene, and mutation (3): a substitution, deletion or insertion at base No. 770 of the CD36 gene.

Preferably, mutation (2) can be a substitution of thymine at base No. 716 of the CD36 gene by guanine (see below). Normal CD36 gene sequence (SEQ ID NO: 42): ex06; mutant gene sequence (SEQ ID NO: 7): t716g. Exon 6 is shown with an underline.

```
ex06     TTGTCTTAAACAGTGACTTTGTTTTTGTAGGCTGCATCCCATATCTATCAAAATCAATTT  60
t716g    TTGTCTTAAACAGTGACTTTGTTTTTGTAGGCTGCATCCCATATCTATCAAAATCAATTT  60
         ************************************************************ ex06     GTTCAAATGATCCTCAATTCACTTATTAACAAGTCAAAATCTTCTATGTTCCAAGTCAGA  120
t716g    GTTCAAATGATCCTCAATTCACTTATTAACAAGTCAAAATCTTCTAGGTTCCAAGTCAGA  120
         ******************************************** *********** ex06     ACTTTGAGAGAACTGTTATGGGGCTATAGGGATCCATTTTTGAGTTTGGTTCCGTACCCT  180
t716g    ACTTTGAGAGAACTGTTATGGGGCTATAGGGATCCATTTTTGAGTTTGGTTCCGTACCCT  180
         ************************************************************ ex06     GTTACTACCACAGTTGGTCTGTTTTATCCTGTAAGTACCAAATATGAATGGCAATATTAT  240
t716g    GTTACTACCACAGTTGGTCTGTTTTATCCTGTAAGTACCAAATATGAATGGCAATATTAT  240
         ************************************************************
```

Preferably, mutation (3) can be an insertion at base No. 770 of the CD36 gene, which generates frameshift, more preferably, an insertion of thymine at base No. 770 of the CD36 gene (see below). Normal CD36 gene sequence (SEQ ID NO: 42): ex06; mutant gene sequence (SEQ ID NO: 6): 770ins. Exon 6 is shown with an underline.

```
ex06     TTGTCTTAAACAGTGACTTTGTTTTTGTAGGCTGCATCCCATATCTATCAAAATCAATTT  60
770ins   TTGTCTTAAACAGTGACTTTGTTTTTGTAGGCTGCATCCCATATCTATCAAAATCAATTT  60
         ************************************************************ ex06     GTTCAAATGATCCTCAATTCACTTATTAACAAGTCAAAATCTTCTATGTTCCAAGTCAGA  120
770ins   GTTCAAATGATCCTCAATTCACTTATTAACAAGTCAAAATCTTCTATGTTCCAAGTCAGA  120
         ************************************************************ ex06     ACTTTGAGAGAACTGTTATGGGGCTATAGGGATCCATTTTT-GAGTTTGGTTCCGTACCC  179
770ins   ACTTTGAGAGAACTGTTATGGGGCTATAGGGATCCATTTTTTGAGTTTGGTTCCGTACCC  180
         ***************************************  ************** ex06     TGTTACTACCACAGTTGGTCTGTTTTATCCTGTAAGTACCAAATATGAATGGCAATATTA  239
770ins   TGTTACTACCACAGTTGGTCTGTTTTATCCTGTAAGTACCAAATATGAATGGCAATATTA  240
         ************************************************************
ex06     T                                                             240
770ins   T                                                             241
         *
```

An example of the mutation within exon 9 is mutation (4): a substitution, deletion or insertion at base No. 970 of the CD36 gene. Preferably, the mutation is a substitution of thymine at base No. 970 of the CD36 gene by cytosine (see below). Normal CD36 gene sequence (SEQ ID NO: 41): ex09; mutant gene sequence (SEQ ID NO: 5): t970c. Exon 9 is shown with an underline.

```
ex09     CTAATCATTTGCCACTCGATTTTTAAACAGATGCAGCCTCATTTCCACCTTTTGTTGAGA  60
t970c    CTAATCATTTGCCACTCGATTTTTAAACAGATGCAGCCTCACTTCCACCTTTTGTTGAGA  60
         ***************************************  ************** ex09     AAAGCCAGGTATTGCAGTTCTTTTCTTCTGATATTTGCAGGTAAGACAGATACTGAAGTA  120
t970c    AAAGCCAGGTATTGCAGTTCTTTTCTTCTGATATTTGCAGGTAAGACAGATACTGAAGTA  120
         ************************************************************ ex09     TAAGTATGCT                                                    130
t970c    TAAGTATGCT                                                    130
         **********
```

An example of the mutation of exon 12 can be mutation (5): a deletion of the nucleotide portion (TTTAGAT) between the 5th base upstream of the 5' terminal of exon 12

(present in the intron) and the 2nd base of exon 12 of the CD36 gene, or a part of the nucleotide portion, which results in the disturbance of normal splicing process, or the complete disappearance of exon 12 from the expressed protein. The deletion of the nucleotide portion (TTTAGAT) between the 5th base upstream of the 5' terminal of exon 12 (present in the intron) and the 2nd base of exon 12 of the CD36 gene is shown below. Normal CD36 gene sequence (SEQ ID NO: 39): ex12; mutant gene sequence (SEQ ID NO: 4): ex12skip. Exon 12 is shown with an underline.

Preferably, mutation (7) can be an insertion at base No. 1457 of the CD36 gene, which results in frameshift, more preferably, an insertion of ttaaagaatctgaagaggaactatat-tgtgcctattctttggc at base No. 1457 (namely, overlapping of the nucleotide portion of base No. 1414 to 1456).

The overlapping of the nucleotide portion of base No. 1414 to 1456of the CD36gene is shown below. Normal CD36 gene sequence (SEQ ID NO: 38): ex13; mutant gene sequence (SEQ ID NO: 2): dup43. Exon 13 is shown with an underline.

```
ex12      TTGGTAATTATTTAGTTGTTCTCTTTTTAGATAACTGGATTCACTTTACAATTTGCAAAA  60
ex12skip  TTGGTAATTATTTAGTTGTTCTCTT-------AACTGGATTCACTTTACAATTTGCAAAA  53
          ***********************       ************************** ex12      CGGCTGCAGGTCAACCTATTGGTCAAGCCATCAGAAAAAATTCAGTGAGTCTCTTGAAAA  120
ex12skip  CGGCTGCAGGTCAACCTATTGGTCAAGCCATCAGAAAAAATTCAGTGAGTCTCTTGAAAA  113
          ************************************************************ ex12      TGGTTATTTTGATA  134
ex12skip  TGGTTATTTTGATA  127
          **************
```

Examples of the mutation of exon 13 include mutation (6): a deletion of the nucleotide portion comprising base No. 1438–1449 of the CD36 gene or a part of base No. 1438 to 1449, mutation (7): a substitution, deletion or insertion at base No. 1457 of the CD36 gene, and mutation (8): a deletion of a nucleotide portion between the 8th base upstream of the 5' terminal of exon 13 (present in the intron) and the 2nd base of exon 13 of the CD36 gene, or a part of the nucleotide portion.

Mutation (6) can be a deletion of the nucleotide portion comprising base No. 1438 to 1449 of the CD36 gene (attgtgcctatt), or a part thereof.

The deletion of the nucleotide portion comprising base No. 1438 to 1449 of the CD36 gene (attgtgcctatt) is shown below. Normal CD36 gene sequence (SEQ ID NO: 38): ex13; mutant gene sequence (SEQ ID NO: 1): del12. Exon 13 is shown with an underline.

```
ex13   AGTTTATATGTTCATAATTATTTTCAACGTATATTACAGAGTATTAAAGAATCTGAAGAG  60
del12  AGTTTATATGTTCATAATTATTTTCAACGTATATTACAGAGTATTAAAGAATCTGAAGAG  60
       ************************************************************ ex13   GAACTATATTGTGCCTATTCTTTGGCTTAATGAGGTTTGTATTTGCAGCTGTTAGTCATT  120
del12  GAACTAT------------CTTTGGCTTAATGAGGTTTGTATTTGCAGCTGTTAGTCATT  108
       *****            *************************************** ex13   AAAA  124
del12  AAAA  112
       ****
```

```
ex13   AGTTTATATGTTCATAATTATTTTCAACGTATATTACAGAGTATTAAAGAATCTGAAGAG    60
dup43  AGTTTATATGTTCATAATTATTTTCAACGTATATTACAGAGTATTAAAGAATCTGAAGAG    60
       ************************************************************ ex13   GAACTATATTGTGCCTATTCTTTGGC----------------------------------    90
dup43  GAACTATATTGTGCCTATTCTTTGGCTTAAAGAATCTGAAGAGGAACTATATTGTGCCTA   120
       ************************* ex13   ---------TTAATGAGGTTTGTATTTGCAGCTGTTAGTCATTAAAA                124
dup43  TTCTTTGGCTTAATGAGGTTTGTATTTGCAGCTGTTAGTCATTAAAA                167
                ***************************************
```

Mutation (8) can be a deletion of the nucleotide portion between the 8th base upstream of the 5' terminal of exon 13 (present in the intron) and the 2nd base of exon 13 of the CD36 gene (tattacagag), or a part of the nucleotide portion, which results in the disturbance of normal splicing process, or a complete disappearance of exon 13 from the expressed protein.

The deletion of the nucleotide portion (tattacagag) between the 8th base upstream of the 5' terminal of exon 13 (present in the intron) and the 2nd base of exon 13 of the CD36 gene is shown below. Normal CD36 gene sequence (SEQ ID NO: 38): ex13; mutant gene sequence: del10 (SEQ ID NO: 3). Exon 13 is shown with an underline.

```
ex13   AGTTTATATGTTCATAATTATTTTCAACGTATATTACAGAGTATTAAAGAATCTGAAGAG    60
del10  AGTTTATATGTTCATAATTATTTTCAACGTA---------TATTAAAGAATCTGAAGAG    50
       *****************************         *************** ex13   GAACTATATTGTGCCTATTCTTTGGCTTAATGAGGTTTGTATTTGCAGCTGTTAGTCATT   120
del10  GAACTATATTGTGCCTATTCTTTGGCTTAATGAGGTTTGTATTTGCAGCTGTTAGTCATT   110
       ************************************************************ ex13   AAAA                                                           124
del10  AAAA                                                           114
       ****
```

An example of the mutation in exon 4 is mutation (9): a substitution, deletion or insertion of a base, preferably a substitution of C by A, at base No. 478 of the CD36 gene (see below).

Normal CD36 gene sequence (SEQ ID NO: 44): ex04; mutant gene sequence: 478CT (SEQ ID NO: 10). Exon 4 is shown with an underline.

```
ex04   CATAACCCAAACTTATTTTCTTTTCCATAGCAAGTTGTCCTCGAAGAAGGTACAATTGCT    60
478CT  CATAACCCAAACTTATTTTCTTTTCCATAGCAAGTTGTCCTCGAAGAAGGTACAATTGCT    60
       ************************************************************ ex04   TTTAAAAATTGGGTTAAAACAGGCACAGAAGTTTACAGACAGTTTTGGATCTTTGATGTG   120
478CT  TTTAAAAATTGGGTTAAAACAGGCACAGAAGTTTACAGACAGTTTTGGATCTTTGATGTG   120
       ************************************************************ ex04   CAAAATCCACAGGAAGTGATGATGAACAGCAGCAACATTCAAGTTAAGCAAAGAGGTCCT   180
478CT  CAAAATCCACAGGAAGTGATGATGAACAGCAGCAACATTCAAGTTAAGCAAAGAGGTTCT   180
       ****************************************************** ex04   TATACGTACAGGTGAGTGAGTGCCCACAAATATGAGACACT                      221
478CT  TATACGTACAGGTGAGTGAGTGCCCACAAATATGAGACACT                      221
       *****************************************
```

Another example of the mutation in exon 5 is mutation (10): a substitution, deletion or insertion at base No. 539 and/or 540, preferably a deletion of AC at base Nos. 539 and 540, in the CD36 gene (see below).

Normal CD36 gene sequence (SEQ ID NO: 43): ex05; mutant gene sequence: 539ACdel (SEQ ID NO: 11). Exon 5 is shown with an underline.

The primers and probes to be used in the detection of mutations of the CD36 gene can be nucleotide fragments comprising at least 12 (for example, 12 to 40) consecutive nucleotides, preferably at least 20 (for example, 20 to 40) consecutive nucleotides, of CD36 mutant genes of the present invention or a compliment thereof, preferably, of the nucleotide sequence selected from the sequences of SEQ ID

```
ex05     TTTGAATTTTGTTTACTGCTGTTTCTTTAGAGTTCGTTTTCTAGCCAAGGAAAATGTAAC  60
539ACdel TTTGAATTTTGTTTACTGCTGTTTCTTTAGAGTTCGTTTTCTAGCCAAGGAAAATGTAAC  60

************************************************************ ex05     CCAGGACGCTGAGGACAACACAGTCTCTTTCCTGCAGCCCAATGGTGCCATCTTCGAACC  120
539ACdel CCAGGACGCTGAGGACA--ACAGTCTCTTTCCTGCAGCCCAATGGTGCCATCTTCGAACC  118

*************** **************************************** ex05     TTCACTATCAGTTGGAACAGAGGCTGACAACTTCACAGTTCTCAATCTGGCTGTGGCAGT  180
539ACdel TTCACTATCAGTTGGAACAGAGGCTGACAACTTCACAGTTCTCAATCTGGCTGTGGCAGT  178

************************************************************ ex05     GAGTAGACAAACAACAAAGTTATCTATT                                 208
539ACdel GAGTAGACAAACAACAAAGTTATCTATT                                 206

****************************
```

An example of the mutation in exon 10 is mutation (11): a substitution, deletion or insertion of a base, preferably an insertion of A, at base No. 1159 of the CD36 gene (see below). Normal CD36 gene sequence (SEQ ID NO: 40): ex10; mutant gene sequence: 1159Ains (SEQ ID NO: 12). Exon 10 is shown with an underline.

NO: 1 through SEQ ID NO: 8 and 10 through 12 or a complement thereof.

The primers to be used for the detection of mutations of the CD36 gene include 5' terminal upstream portions and 3' site downstream portions of each exon and complementary sequences thereof, but they are not restricted to these por-

```
ex10     TGGAATGCAGCTCTTTTTTCTCTGTATTTAGGTCAATCTATGCTGTATTTGAATCCGACG  60
1159Ains TGGAATGCAGCTCTTTTTTCTCTGTATTTAGGTCAATCTATGCTGTATTTGAATCCGACG  60

************************************************************ ex10     TTAATCTGAAAGGAATCCCTGTGTATAGATTTGTTCTTCCATCCAAGGCCTTTGCCTCTC  120
1159Ains TTAATCTGAAAGGAATCCCTGTGTATAGATTTGTTCTTCCATCCAAGGCCTTTGCCTCTC  120

************************************************************ ex10     CAGTTGAAAACCCAGACAACTATTGTTTCTGCACAGAAAAAATTATCTC-AAAAAATTGT  179
1159Ains CAGTTGAAAACCCAGACAACTATTGTTTCTGCACAGAAAAAATTATCTCAAAAAAATTGT  180

************************************************* **********
         ********* ex10     ACATCATATGGTGTGCTAGACATCAGCAAATGCAAAGAAGGTGAGTAAATAACCTCAGTA  239
1159Ains ACATCATATGGTGTGCTAGACATCAGCAAATGCAAAGAAGGTGAGTAAATAACCTCAGTA  240

************************************************************ ex10     GCACAGTCCAT                                                  250
1159Ains GCACAGTCCAT                                                  251

***********
```

The term "reagent for detecting a mutation of the CD36 gene" as used herein refers to primers, probes and restriction enzymes which are required for the detection of specified or unspecified mutations in the CD36 gene, reagents used in sequence determination methods for nucleic acids such as the Maxam-Gilbert Method and the Chain Terminator Method, and the CD36 gene and CD36 mutant genes used as templates for the amplification of nucleotide fragments. These reagents are used in the judgement of diseases caused by abnormal lipid metabolism, or the onset possibility of the diseases, according to the present invention.

tions. Preferably, the primers can be the nucleotide fragments depicted in SEQ ID NOS: 13–37 and a complement thereof.

The probes to be used for the detection of mutations of the CD36 gene can be selected from the nucleotide fragments depicted in SEQ ID NOS: 1 to 8 and 10 to 12 and a complement thereof. The probes can be labeled using conventional methods.

The primer pair according to the present invention consists of two primers for detecting a mutation of the CD36 gene. The primer pair may consist of a nucleotide fragment consisting of at least 12 (for example, 12 to 40) consecutive nucleotides, preferably at least 20 (for example, 20 to 40) consecutive nucleotides, of the CD 36 gene or the CD36 mutant gene, and a nucleotide fragment consisting of at least 12 (for example, 12 to 40) consecutive nucleotides, preferably at least 20 (for example, 20 to 40) consecutive nucleotides, of a complement of the CD 36 gene or the CD36 mutant gene. Examples of the primer pair include nucleotide sequences of SEQ ID NOS: 13 and 14, nucleotide sequences of SEQ ID NOS: 15 and 16, nucleotide sequences of SEQ ID NOS: 17 and 18, nucleotide sequences of SEQ ID NOS: 19 and 20, nucleotide sequences of SEQ ID NOS: 21 and 22, nucleotide sequences of SEQ ID NOS: 23 and 24, nucleotide sequences of SEQ ID NOS: 25 and 26, nucleotide sequences of SEQ ID NOS: 27 and 28, nucleotide sequences of SEQ ID NOS: 29 and 30, nucleotide sequences of SEQ ID NOS: 31 or 32 and 33, nucleotide sequences of SEQ ID NOS: 34 and 35, nucleotide sequences of SEQ ID NOS: 36 and 37.

In the present invention, accuracy of the judgement can be improved by detecting two or more mutations selected from (1) through (11) in combination.

Accordingly, it should be understood that the embodiment of the detection of two or more mutations selected from (1) through (11) in combination is within the scope of the method and kit according to the present invention.

The diagnosis and judgment of diseases caused by lipid metabolism abnormality can be carried out by detecting a mutation of the CD36 gene.

The presence of the mutation of the CD36 gene indicates a predisposition to diseases caused by abnormal lipid metabolism.

The detection of the mutation of the CD36 gene can be carried out by hybridizing the nucleotide sequence selected from SEQ ID NO.1 to 8 and 10 to 12 or a complement thereof, or a nucleotide probe comprising their mutation portion with a nucleic acid sample isolated from a subject and then detecting the presence of a hybridization complex. The presence of the hybridization complex indicates the presence of the mutation. The hybridization complex can be detected by capturing the target nucleotides on the immobilized probe and detecting the presence of the labeled nucleic acid sample. The hybridization complex can also be determined by detecting the presence of an amplified product by PCR or the like, specifically by preparing a nucleotide probe and another nucleotide fragment of the CD36 gene and amplifying a nucleic acid sample by PCR using the above nucleotide fragment as a primer pair. The presence of the amplified product indicates the presence of the mutation.

The detection of the mutation of the CD36 gene can also be carried out by amplifying a nucleic acid sample isolated from a subject and a standard nucleic acid sample with a primer pair for detecting a mutation of the CD36 gene comprising a nucleotide fragment consisting of at least 12 (for example, 12 to 40) consecutive.nucleotides, preferably at least 20 (for example, 20 to 40) consecutive nucleotides, of the CD36 mutant gene nucleotide sequence or a complement thiereof; heat-denaturing and then cooling the resulting amplified products so as to generate the substitution of the complementary strands; and detecting the degree of the substitution of the complementary strands. The substitution of the complementary strands of the standard nucleic acid sample isolated from a wild type indicates the presence of a wild type gene. The substitution of the complementary strands of the standard nucleic acid sample isolated from a mutant type indicates the presence of a mutant type gene. The details of the diagnosis and determination of the diseases are described after.

The diagnosis and judgment of diseases caused by lipid metabolism abnormalitycan be carried out by detecting unspecified or specified mutations in the CD36 gene.

By detecting unspecified mutation, mutant genes can be analyzed throughout the CD36 gene. If a test sample is revealed to have a mutation of the CD36 gene, the sample is diagnosed or judged as being from a patient suffering from diseases caused by lipid metabolism abnormalityor a patient in danger of incurring such diseases.

As for the detection of specified mutations, sufficient diagnosis and assessment can be done by detecting necessary specified mutations in the cases where a sufficient detection rate can be expected simply by analyzing the presence or absence of certain specified mutations or a marked correlation exists between a certain specified mutation and symptoms. Thus, a patient can be diagnosed or assessed to have diseases caused by lipid metabolism abnormalityor be in danger of incurring such diseases if the test sample from the patient is revealed to have mutations (1) to (11).

Detection of Unspecified Mutations

Examples of the methods for detecting unspecified mutations include PCR-SSCP, PCR-DGGE, the mismatch cleaving method using RNase and the PCR-PHFA method (I). Detection of unspecified mutations by the PCR-PHFA method (I) (U.S. Pat. No. 5,688,643) used in the present invention will be explained as follows.

In the PCR-PHFA method (I), a target gene having the wild type sequence is amplified by PCR using unlabeled primers which can specifically amplify this region to obtain an unlabeled standard DNA. On the other hand, the same region of a test sample is amplified using labeled primers of the same sequence to obtain a labeled sample DNA which has labels on both ends. One of the labeled primers has a label which can adhere to a solid phase and the other primer has a detectable label.

The labeled sample DNA and the unlabeled standard DNA in great excess (normally 10 to 30 times) over the labeled sample DNA are mixed. The admixture is held at a temperature high enough to induce heat denaturation (normally 98° C.) for about 10 minutes, then gradually cooled to a temperature low enough to complete annealing (normally 70° C.) with a gentle temperature gradient (normally 1° C./3–10 minutes). In this process, if the test sample is the wild-type homozygote, the substitution of the complementary strands occurs between the labeled DNA and the unlabeled DNA because the sequences of the labeled sample DNA and the unlabeled standard DNA are completely the same. Thus, the original molecules having the labels on both ends are reconstructed simply at the mathematical probability in proportion to the level of excessiveness of the unlabeled DNA. On the other hand, a slight difference in the sequences is recognized in the step of the temperature gradient if the test sample has sequences which are different from the wild type for both alleles in the target region. Thus, the original molecule having labels on both ends is reconstructed with high efficiency. Further, if the test sample has the wild-type sequence for one allele and a sequence different from the wild type for the other allele, the labeled sample DNA derived from the wild-type allele is poorly reconstructed while the labeled DNA derived from the allele having a sequence different from the wild type is efficiently reconstructed. Thus, the labeled DNA can be reconstructed with efficiency level between the above-mentioned two cases.

DNA can be labeled with biotin which can adhere to a solid phase. The labeled DNA can be captured on a microplate on which streptavidin is immobilized. Also, DNP (dinitrophenyl group) is used as a detectable label, alkaline phosphatase-labeled anti-DNP antibody is bound, then the target can be detected by yellow coloring using pNPP (p-nitrophenylphosphate) as a coloring substrate. In this system, the alkaline phosphatase-labeled anti-DNP antibody is dispensed to the microplate on which streptavidin is immobilized, to which a solution, in which the labeled sample DNA is annealed under the above-mentioned conditions after mixing with the unlabeled standard DNA, is added. The both-end-labeled DNA adheres to the microplate with the label of one end, and the alkaline phosphatase-labeled anti-DNP antibody binds to the label of the other end. After washing, coloring occurs by adding pNPP as a coloring substrate. The intensity of this coloring depends on the amount of the both-end-labeled DNA present on the solid phase, namely the rate of reconstruction of the both-end-labeled DNA. In this manner, it can be judged whether the alleles of the original test sample are both wild type, one wild type and the other different from the wild type, or both different from the wild type.

Since the extent of distinction between the wild-type sequence and non-wild-type sequence during annealing process varies depending on the chain length and nucleotide sequence of each exon, the judgement can be done by setting appropriate cutoff values for each region to be analyzed.

Detection of Specified Mutations

Examples of the methods for detecting specified mutant genes include the ASO method, SSP method, LCR method and PHFA method (2). The PHFA method (WO98/02574) used in the present invention will be explained as follows. Methods of detecting specified mutations in genes of C478T mutation of exon 4, 539AC deletion of exon 5 and 1159A insertion of exon 10 will be explained.

A chromosomal DNA having the CD36 gene (wild type) sequence is amplified by PCR using primers for exon amplification. The resulting DNA is introduced into pT7Blue-T vector, after which base sequences are confirmed and a plasmid having the wild-type sequence is obtained. On the other hand, a chromosomal DNA having a CD36 mutant gene is amplified using the same primers and introduced into the same vector, after which base sequences are confirmed and a plasmid having the mutant gene is obtained.

Using the wild-type and mutant-type plasmids as templates, wild-type and mutant-type labeled standard DNA sequences are obtained by the amplification using labeled primers for exon amplification (having the same sequences as the unlabeled primers for exon amplification). On the other hand, an unlabeled sample DNA is prepared by amplifying a sample DNA using unlabeled primers for exon amplification.

To the labeled standard DNA, the unlabeled sample DNA in great excess (normally 10 to 30 times) over the labeled standard DNA is added. Heat denaturation and annealing are carried out in the same manner as described above in the section for the detection of unspecified mutations. The results show that if the test sample has the same sequence as the sequence of the labeled standard DNA, the probability of the reconstruction of the labeled DNA is mathematical and decreases in proportion of the level of excessiveness of the unlabeled DNA. On the other hand, if the test sample has a sequence different from the labeled standard DNA, the original labeled standard DNA is reconstructed with high efficiency. This difference can be detected by the above-mentioned coloring system. Thus, it can be judged whether the test sample has a specified mutant gene or not. Since the chain length and base sequence of each exon to be analyzed is different, the judgement can be done by setting appropriate cutoff values for each region to be analyzed.

In this manner, various unspecified mutant genes have been revealed. Of these mutant genes, sequences are confirmed as novel mutant genes for those in which the mutation is new in the corresponding exon and those in which the sequence of the mutated gene is different from those previously reported for the corresponding exons. These mutant genes are added to the group of specified mutant genes to be detected as new mutant genes which can be used for further diagnosis and judgement.

"Diseases caused by abnormal lipid metabolism" in the present invention include arterial sclerosis, hyperlipidemia, angina pectoris, cardiomyopathy, juvenile sudden death, and accidents in surgical operations.

Idiopathic cardiomyopathy, or simply cardiomyopathy, was defined in 1980 as "a myocardial disease with cause unknown" at the Cardiomyopathy Committee of the World Health Organization/World Academic Federation for Cardiac Diseases and was redefined in 1995 as "a myocardial disease associated with cardiac malfunctions", and right ventricular arrhythmogenic cardiomyopathy was added to this group in addition to conventional hypertrophic, ectatic and constraint cardiomyopathy. Symptoms of cardiomyopathy, cause of which is so far said to be unknown, are often observed in complete CD36 deficiency, and this gene is considered to be one of the causative genes for cardiomyopathy (hypertrophic or ectatic type). Although juvenile cardiomyopathy is often difficult to diagnose by using conventional test methods such as myocardial ultrasonic tomography, the judging method according to the present invention can make it possible to diagnose cardiomyopathy before birth and immediately after birth. Furthermore, abnormality in genes of children can be found by investigating genes of their parents. In particular, the judging method of the present invention is effective for assessing the development and prognosis of ectatic cardiomyopathy in which heart transplant is the sole choice of the treatment.

Juvenile sudden death often occurs in apparently healthy children during or immediately after exercise. After investigation, the present inventors found that sudden death in infancy and childhood occurs in a relatively high frequency in families of patients with CD36 deficiency.

A probable mechanism to lead sudden death is suggested as follows. Alternative energy sources such as glucose are used under the conditions in which there are certain disorders in the metabolism of long chain fatty acids, a major source of energy in the myocardium. Accordingly, if disorders in glucose utilization (for example, hypoglycemia, excessive exercise with an empty stomach, inappetence caused by infectious disease, diarrhea, vomiting, fever and deficiency in vitamin B1 which is necessary for sugar metabolism) additionally occur under the conditions in which there are certain disorders in incorporation of long chain fatty acids, serious events such as fatal pump malfunction and arrhythmia can be readily induced. These serious events including juvenile sudden death can be prevented if the CD36 gene is analyzed after birth or before school age to know in advance the presence of abnormality in the CD36 gene and to provide appropriate instructions. Furthermore, when a couple having a family history (genetical history) of cause-unknown cardiac diseases want to have a baby, their genes can be analyzed to find possible abnormalities in the CD36 gene, which may be useful for the future plan of the couple.

Owing to development in surgical technology, cardiac operations are being performed extensively. However, if the patients have disorders in incorporation of long chain fatty acids, there are some potential problems in myocardial protection and post-operational management. In fact, poor prognoses after operation have been reported in patients with CD36 deficiency. Accordingly, the analysis of the CD36 gene is considered to be useful to prevent undesirable events during and after the operation in the case where a large scale operation as well as a cardiac operation is necessary.

EXAMPLE

The present inventors studied myocardial scintigram of 6970 subjects having a history of cardiac diseases or in danger of incurring such diseases, using radiolabeled iodine-labeled 15-(p-iodophenyl)-3-R,S-methylpentagecanoic acid (BMIPP) which is analogous to a long chain fatty acid. As a result, 33 subjects (0.47%) were found to completely lack the ability to incorporate fatty acid into the myocardium (date not shown). Chromosomal DNAs for 28 of the 33 subjects were prepared. Separately, chromosomal DNAs were prepared from 13 subjects having heart diseases in which fatty acid incorporation into the myocardium was not observed. CD36 protein expression in platelets and monocytes was studied for the total of 41 test samples using flow cytometry. As a result, it was revealed that neither platelets nor monocytes expressed the CD36 protein in all cases (date not shown).

The present inventors prepared chromosomal DNAs of these 41 samples and analyzed gene mutations in their entire exon regions. The results showed that all of the 41 samples tested were homozygous for C478T mutation in exon 4 or had two kinds of mutant genes (data not shown).

Further, since there were certain regions where incorporation of long chain fatty acids into the myocardium was partially not observed even in subjects who were heterozygous for this mutation having the mutant gene only on one allele (Tanaka et al., J. Mol. Cell Cardiol., Vol. 29, 121–127 (1997)), it is suggested that there may be a certain abnormality in energy supply to the heart.

In the following Examples, the 41 samples were tested. In addition, tissue samples were removed by the Batista operation from 27 cardiomyopathy patients suffering from severe heart failure, chromosomal DNAS were prepared from the tissues for the detection of CD36 gene mutations, and the detection of CD36 gene mutations were attempted.

Example 1
Detection of Unspecified Mutations in the CD36 Gene

A method of detecting unspecified mutations in the CD36 gene will be explained in detail as follows. Although mutations in exons are exemplified in this example, analysis can be carried out in the same manner with mutations in regions, such introns, regions associated with transcription regulations including promoters upstream of the gene and non-coding regions downstream of the gene. Further, the PCR-PHFA method (I) is used for detecting unspecified mutations in the following description, but any other methods which can detect unspecified mutant genes, such as SSCP, PGGE, and the mismatch cleaving method can be used for the analysis. Also, primer sequences used in PCR can be any sequences which specifically amplify targeted gene regions and are not restricted to the sequences used in this example.

(1) Detection of Unspecified Mutations in Exon 3

A method of detecting unspecified mutations in exon 3 will be explained in detail as follows.

(i) Preparation of Wild-type Unlabeled Standard DNA

A chromosomal DNA having a sequence for the wild-type CD36 gene was extracted from peripheral blood lymphocytes using a QIAamp blood kit (QIAGEN).

CD36-3U: 5'-OH-TTCTGTTTTATGATCTCTTTCTAAT (SEQ ID NO: 13)

CD36-3L: 5'-OH-AATGAGAGGATATTCTTTGACTAC (SEQ ID NO: 14)

A solution for PCR (100 µl) was prepared by adding 200 µM dNTPs, 2.5 mM $MgCl_2$, 2.5 units Ampli Taq Gold (Perkin Elmer-ABI) using 10 pmol each of unlabeled primers for CD36 exon 3 amplification having the sequences above using 100 ng of the extracted chromosomal DNA as a template using a buffer solution for Ampli Taq Gold. After pretreatment at 96° C. for 12 minutes, PCR was performed for 40 cycles of heat denaturation (94° C., 30 seconds), annealing (50° C., 60 seconds) and elongation (72° C., 60 seconds) using Gene Amp PCR System 9600 (Perkin Elmer-ABI). The resulting amplification product (50 µl) was subjected to 3% agarose gel electrophoresis to extract DNA having a chain length of 269 bp from a targeted band. This DNA was introduced into the pT7Blue-T vector to transform *Escherichia coli*. A plasmid was prepared from the resultant transformant, its base sequence was confirmed, then the plasmid was named pEX03W.

A solution for PCR containing the above-mentioned components was prepared using 10 pg of plasmid pEX04W as a template and 10 pmol each of the above-mentioned unlabeled primers for exon 3 amplification. PCR amplification was performed under the above-mentioned cycle conditions to obtain the exon 3 wild-type unlabeled standard DNA.

(ii) Preparation of Labeled Sample DNA

Bio-CD36-3U: 5'-biotin-TTCTGTTTTATGATCTCTTTCTAAT (SEQ ID NO: 13)

Bio-CD36-3L: 5'-DNP-AATGAGAGGATATTCTTTGACTAC (SEQ ID NO: 14)

Amplification was performed using the above-mentioned PCR device under the above-mentioned cycle conditions using 30 ng of chromosomal DNA extracted from peripheral blood lymphocytes of a patient using a QIAamp blood kit as a template by adding 200 µM dNTPs containing 3 pmol each of the above-mentioned labeled primers for CD36 exon 4 amplificationl unit Ampli Taq Gold (Perkin Elmer-ABI) and 2.5 mM $MgCl_2$ in 30 µl of buffer solution for Ampli Taq Gold to obtain the labeled sample DNA.

(iii) Annealing Reaction by Temperature Gradient

A solution (30 µl) containing 1 µl of the labeled sample DNA and 15 µl of the unlabeled standard DNA at a final concentration of 3.3×SSC (20×SSC: 0.3 M sodium citrate, pH 7.0, 0.3 M sodium chloride) was prepared. After heat denaturation using the Gene Amp PCR System 9600 (Perkin Elmer-ABI), annealing was carried out by temperature gradient. That is, after heating at 98° C. for 10 minutes, the temperature was gradually lowered from 98° C. to 70C at a rate of 1° C./10 minutes.

To prepare a coloring positive control, the heat denaturation and temperature-gradient annealing were performed with a solution prepared in the same manner as described above except that a buffer solution for Ampli Tag Gold (15 µl) was added in place of the unlabeled standard DNA.

(iv) Coloring Reaction

Coloring was performed with the annealing solution (20 µl) prepared in (iii) using the system of ED-PCR (U.S. Pat. No. 2,786,857). For each test sample, the ratio of the absorbance for the coloring positive control and absorbance for the solution with the unlabeled standard DNA added was calculated, and the presence or absence of mutations was judged using the percentage of the reconstruction of the labeled DNA as an index.

(2) Detection of Unspecified Mutations in Exon 4

Detection of unspecified mutations in exon 4 was carried out in the same manner as described for exon 3 except that primers having the following sequences were used, the resultant PCR amplification product had a chain length of 221 bp, and the resulting plasmid having the wild-type sequence was pEX04W.

CD36-4U: 5'-OH-CATAACCCAAACTTATTTTCTTTTCC (SEQ ID NO: 15)

CD36-4L: 5'-OH-AGTGTCTCATATTTGTGGGCACTCA (SEQ ID NO: 16)

Bio-CD36-4U: 5'-biotin-CATAACCCAAACTTATTTTCTTTTCC (SEQ ID NO: 15)

DNP-CD36-4L: 5'-DNP-AGTGTCTCATATTTGTGGGCACTCA (SEQ ID NO: 16)

The results of the detection of unspecified mutations in exon 4 are shown in Table 1.

(3) Detection of Unspecified Mutations in Exon 5

Detection of unspecified mutations in exon 5 was carried out in the same manner as described for exon 3 except that primers having the following sequences were used, the resultant PCR amplification product had a chain length of 208 bp, and the resulting plasmid having the wild-type sequence was pEX05W.

CD36-5U: 5'-OH-TTTGAATTTTGTTTACTGCTGTTTC (SEQ ID NO: 17)

CD36-5L: 5'-OH-AATAGATAACTTTGTTGTTTGTCTAC (SEQ ID NO: 18)

Bio-CD36-5U: 5'-biotin-TTTGAATTTTGTTTACTGCTGTTTC (SEQ ID NO: 17)

DNP-CD36-5L: 5'-DNP-AATAGATAACTTTGTTGTTTGTCTAC (SEQ ID NO: 18)

The results of the detection of unspecified mutations in exon 5 are shown in Table 1.

(4) Detection of Unspecified Mutations in Exon 6

Detection of unspecified mutations in exon 6 was carried out in the same manner as described for exon 3 except that primers having the following sequences were used, the resultant PCR amplification product had a chain length of 240 bp, and the resulting plasmid having the wild-type sequence was pEX06W.

CD36-6U: 5'-OH-TTGTCTTAAACAGTGACTTTGTTTT (SEQ ID NO: 19)

CD36-6L: 5'-OH-ATAATATTGCCATTCATATTTGGTA (SEQ ID NO: 20)

Bio-CD36-6U: 5'-biotin-TTGTCTTAAACAGTGACTTTGTTTT (SEQ ID NO: 19)

DNP-CD36-6L: 5'-DNP-ATAATATTGCCATTCATATTTGGTA (SEQ ID NO: 20)

(5) Detection of Unspecified Mutations in Exon 7

Detection of unspecified mutations in exon 7 was carried out in the same manner as described for exon 3 except that primers having the following sequences were used, the resultant PCR amplification product had a chain length of 152 bp, and the resulting plasmid having the wild-type sequence was pEX07W.

CD36-7U: 5'-OH-AAGTAACATTTTCCCATACATATAT (SEQ ID NO: 21)

CD36-7L: 5'-OH-CATACATGCACATTTTACCAGAATA (SEQ ID NO: 22)

Bio-CD36-7U: 5'-biotin-AAGTAACATTTTCCCATACATATAT (SEQ ID NO: 21)

DNP-CD36-7L: 5'-DNP-CATACATGCACATTTTACCAGAATA (SEQ ID NO: 22)

(6) Detection of Unspecified Mutations in Exon 8

Detection of unspecified mutations in exon 8 was carried out in the same manner as described for exon 3 except that primers having the following sequences were used, the resultant PCR amplification product had a chain length of 107 bp, and the resulting plasmid having the wild-type sequence was pEX08W.

CD36-8U: 5'-OH-TGTTTAATTCATTGTCTTTTTCTATT (SEQ ID NO: 23)

CD36-8L: 5'-OH-CTGTGATGACCACAAAACAAATATT (SEQ ID NO: 24)

Bio-CD36-8U: 5'-biotin-TGTTTAATTCATTGTCTTTTTCTATT (SEQ ID NO: 23)

DNP-CD36-8L: 5'-DNP-CTGTGATGACCACAAAACAAATATT (SEQ ID NO: 24)

(7) Detection of Unspecified Mutations in Exon 9

Detection of unspecified mutations in exon 9 was carried out in the same manner as described for exon 3 except that primers having the following sequences were used, the resultant PCR amplification product had a chain length of 130 bp, and the resulting plasmid having the wild-type sequence was pEX09W.

CD36-9U: 5'-OH-CTAATCATTTGCCACTCGATTTTTA (SEQ ID NO: 25)

CD36-9L: 5'-OH-AGCATACTTATACTTCAGTATCTGT (SEQ ID NO: 26)

Bio-CD36-9U: 5'-biotin-CTAATCATTTGCCACTCGATTTTTA (SEQ ID NO: 25)

DNP-CD36-9L: 5'-DNP-AGCATACTTATACTTCAGTATCTGT (SEQ ID NO: 26)

(8) Detection of Unspecified Mutations in Exon 10

Detection of unspecified mutations in exon 10 was carried out in the same manner as described for exon 3 except that primers having the following sequences were used, the resultant PCR amplification product had a chain length of 250 bp, and the resulting plasmid having the wild-type sequence was pEX10W.

CD36-10U: 5'-OH-TGGAATGCAGCTCTTTTTTCTCTGT (SEQ ID NO: 27)

CD36-10L: 5'-OH-ATGGACTGTGCTACTGAGGTTATTT (SEQ ID NO: 28)

Bio-CD36-10U: 5'-biotin-TGGAATGCAGCTCTTTTTTCTCTGT (SEQ ID NO: 27)

DNP-CD36-10L: 5'-DNP-ATGGACTGTGCTACTGAGGTTATTT (SEQ ID NO: 28)

The results of the detection of unspecified mutations in exon 10 are shown in Table 1.

(9) Detection of Unspecified Mutations in Exon 11

Detection of unspecified mutations in exon 11 was carried out in the same manner as described for exon 3 except that primers having the following sequences were used, the resultant PCR amplification product had a chain length of 179 bp, and the 25 resulting plasmid having the wild-type sequence was pEX11W.

CD36-11U: 5'-OH-TTCCAATTGACTCTTAAAACTTGTC (SEQ ID NO: 29)

CD36-11L: 5'-OH-CCAAATCAGATCAATAAGGTGTTTT (SEQ ID NO: 30)
Bio-CD36-11U: 5'-biotin-TTCCAATTGACTCTTAAAACTTGTC (SEQ ID NO: 29)
DNP-CD36-11L: 5'-DNP-CCAAATCAGATCAATAAGGTGTTTT (SEQ ID NO: 30)

(10) Detection of Unspecified Mutations in Exon 12

Detection of unspecified mutations in exon 12 was carried out in the same manner as described for exon 3 except that primers having the following sequences were used, the resultant PCR 35 amplification product had a chain length of 134 bp, and the resulting plasmid having the wild-type sequence was pEX12W.

CD36-12U: 5'-OH-TTGGTAATTATTTAGTTGTTCTCTT (SEQ ID NO: 31) or
CD36-12U2: 5'-OH-TTGGTAATTATTTAGTTGTTCTCTTTTTAG (SEQ ID NO: 32)
CD36-12L2: 5'-OH-TATCAAAATAACCATTTTCAAGAGACTCAC (SEQ ID NO: 33)
Bio-CD36-12U: 5'-biotin-TTGGTAATTATTTAGTTGTTCTCTT (SEQ ID NO: 31) or
Bio-CD36-12U2: 5'-biotin-TTGGTAATTATTTAGTTGTTCTCTTTTTAG (SEQ ID NO: 32)
DNP-CD36-12L2: 5'-DNP-TATCAAAATAACCATTTTCAAGAGACTCAC (SEQ ID NO: 33)

(11) Detection of Unspecified Mutations in Exon 13

Detection of unspecified mutations in exon 13 was carried out in the same manner as described for exon 3 except that primers having the following sequences were used, the resultant PCR amplification product had a chain length of 122 bp, and the resulting plasmid having the wild-type sequence was pEX13W.

CD36-13U3: 5'-OH-AGTTTATATGTTCATAATTATTTTCAACGT (SEQ ID NO: 34)
CD36-13L2: 5'-OH-TTTTAATGACTAACAGCTGCAAATACAAAC (SEQ ID NO: 35)
Bio-CD36-13U3: 5'-biotin-AGTTTATATGTTCATAATTATTTTCAACGT (SEQ ID NO: 34)
DNP-CD36-13L2: 5'-DNP-TTTTAATGACTAACAGCTGCAAATACAAAC (SEQ ID NO: 35)

(12) Detection of Unspecified Mutations in Exon 14

Detection of unspecified mutations in exon 14 was carried out in the same manner as described for exon 3 except that primers having the following sequences were used, the resultant PCR amplification product had a chain length of 225 bp, and the resulting plasmid having the wild-type sequence was pEX14W. This PCR amplification product contains about 30 bases downstream of the termination codon present in exon 14 and does not contain further downstream regions.

CD36-14U: 5'-OH-AAATAATGTTGATTATTAACTTGAT (SEQ ID NO: 36)
CD36-14L: 5'-OH-TGAAGCAATATTTTTTGGTACATAC (SEQ ID NO: 37)
Bio-CD36-14U: 5'-biotin-AAATAATGTTGATTATTAACTTGAT (SEQ ID NO: 36)
DNP-CD36-14L: 5'-DNP-TGAAGCAATATTTTTTGGTACATAC (SEQ ID NO: 37)

TABLE 1

Results of the detection of unspecified mutations in exons 4, 5 and 10

| | exon #4 | | | | exon #5 | | | | exon #10 | | | |
|---|---|---|---|---|---|---|---|---|---|---|---|---|
| | H2O | wild | Index | Judgement | H2O | wild | Index | Judgement | H2O | wild | Index | Judgement |
| #301 | 1.205 | 0.317 | 26.3 | hetero | 1.291 | 0.120 | 9.3 | wild | 1.367 | 0.108 | 7.9 | wild |
| #302 | 1.186 | 0.071 | 6.0 | wild | 1.132 | 0.098 | 8.7 | wild | 1.335 | 0.092 | 6.9 | wild |
| #303 | 1.042 | 0.055 | 5.3 | wild | 1.112 | 0.071 | 6.4 | wild | 1.188 | 0.072 | 6.1 | wild |
| #304 | 1.163 | 0.073 | 6.3 | wild | 1.190 | 0.102 | 8.6 | wild | 1.252 | 0.080 | 6.4 | wild |
| #305 | 1.013 | 0.051 | 5.0 | wild | 1.082 | 0.074 | 6.8 | wild | 1.208 | 0.067 | 5.6 | wild |
| #306 | 1.024 | 0.054 | 5.3 | wild | 1.092 | 0.080 | 7.3 | wild | 1.210 | 0.064 | 5.3 | wild |
| #307 | 1.072 | 0.558 | 52.1 | hetero | 1.152 | 0.100 | 8.7 | wild | 1.267 | 0.081 | 6.4 | wild |
| #308 | 1.181 | 0.080 | 6.8 | wild | 1.220 | 0.103 | 8.5 | wild | 1.270 | 0.075 | 5.9 | wild |
| #309 | 0.861 | 0.031 | 3.6 | wild | 0.971 | 0.045 | 4.6 | wild | 1.111 | 0.051 | 4.6 | wild |
| #310 | 0.670 | 0.099 | 14.8 | hetero | 0.544 | 0.011 | 2.0 | wild | 0.847 | 0.023 | 2.7 | wild |
| #311 | 0.949 | 0.045 | 4.8 | wild | 1.083 | 0.096 | 8.9 | wild | 1.214 | 0.062 | 5.1 | wild |
| #312 | 0.897 | 0.060 | 6.7 | wild | 0.803 | 0.036 | 4.5 | wild | 1.066 | 0.052 | 4.9 | wild |
| #313 | 1.105 | 0.257 | 23.3 | hetero | 1.168 | 0.108 | 9.3 | wild | 1.211 | 0.083 | 6.9 | wild |
| #314 | 0.976 | 0.202 | 20.7 | hetero | 1.087 | 0.343 | 31.6 | hetero | 1.147 | 0.064 | 5.6 | wild |
| #315 | 1.183 | 0.298 | 25.2 | hetero | 1.252 | 0.131 | 10.5 | wild | 1.306 | 0.215 | 16.5 | hetero |
| #316 | 1.125 | 0.223 | 19.8 | hetero | 1.236 | 0.113 | 9.2 | wild | 1.287 | 0.189 | 14.7 | hetero |
| #317 | 0.898 | 0.499 | 55.6 | homo | 1.298 | 0.097 | 7.5 | wild | 1.106 | 0.059 | 5.3 | wild |
| #318 | 1.117 | 0.670 | 60.0 | homo | 1.492 | 0.143 | 9.6 | wild | 1.262 | 0.092 | 7.3 | wild |
| #319 | 0.821 | 0.397 | 48.4 | homo | 1.047 | 0.054 | 5.2 | wild | 0.966 | 0.045 | 4.7 | wild |
| #320 | 0.904 | 0.470 | 52.0 | homo | 0.768 | 0.018 | 2.4 | wild | 1.031 | 0.082 | 8.0 | wild |
| #321 | 0.934 | 0.471 | 50.4 | homo | 1.472 | 0.133 | 9.0 | wild | 1.141 | 0.072 | 6.3 | wild |
| #322 | 0.946 | 0.517 | 54.7 | homo | 1.435 | 0.141 | 9.8 | wild | 1.125 | 0.077 | 6.9 | wild |
| #323 | 0.965 | 0.048 | 5.0 | wild | 1.302 | 0.100 | 7.7 | wild | 0.898 | 0.032 | 3.6 | wild |
| #324 | 1.018 | 0.057 | 5.6 | wild | 1.337 | 0.097 | 7.3 | wild | 1.113 | 0.064 | 5.8 | wild |
| #325 | 1.001 | 0.538 | 53.8 | homo | 1.310 | 0.139 | 10.6 | wild | 1.189 | 0.078 | 6.6 | wild |
| #326 | 1.040 | 0.052 | 5.0 | wild | 1.216 | 0.114 | 9.4 | wild | 1.174 | 0.078 | 6.7 | wild |
| #327 | 1.050 | 0.053 | 5.1 | wild | 1.270 | 0.137 | 10.8 | wild | 1.083 | 0.074 | 6.8 | wild |

TABLE 1-continued

Results of the detection of unspecified mutations in exons 4, 5 and 10

| | exon #4 | | | | exon #5 | | | | exon #10 | | | |
|---|---|---|---|---|---|---|---|---|---|---|---|---|
| | H2O | wild | Index | Judgement | H2O | wild | Index | Judgement | H2O | wild | Index | Judgement |
| #328 | 1.113 | 0.067 | 6.0 | wild | 1.318 | 0.158 | 12.0 | wild | 1.020 | 0.051 | 5.0 | wild |
| #329 | 1.021 | 0.052 | 5.1 | wild | 1.173 | 0.104 | 8.9 | wild | 1.047 | 0.065 | 6.2 | wild |
| #330 | 1.127 | 0.060 | 5.3 | wild | 1.305 | 0.146 | 11.2 | wild | 1.173 | 0.090 | 7.7 | wild |
| Wild | 1.135 | 0.075 | 6.6 | wild | 1.353 | 0.180 | 13.3 | wild | 1.190 | 0.095 | 8.0 | wild |
| Hetero | 1.081 | 0.306 | 28.3 | hetero | 1.257 | 0.425 | 33.8 | hetero | 1.281 | 0.246 | 19.2 | hetero |

Wild: wild type. Hetero: mutations exist only in one allele. Homo: mutations exist on both alleles.

The judgement was made according to the following cutoff values.

Exon 4 Wild: Index<10, heterozygote: 10≦Index<30, homozygote (mutant): 30≦Index.
Exon 5 Wild: Index<15, heterozygote: 15≦Index<40, homozygote (mutant): 40≦Index.
Exon 10 Wild: Index<10, heterozygote: 10≦Index<30, homozygote (mutant): 30≦Index.

Example 2

Detection of Specified Mutations in the CD36 Gene

A method of detecting unspecified mutations in the CD36 gene will be explained in detail as follows. Although mutations present in exons are exemplified in this example, analyses can be made in the same manner also for mutations in other regions, such as introns, regions associated with transcription regulations including promoters upstream of the gene and non-coding regions downstream of the gene. Further, although the PCR-PHFA method (II) is used for detecting specified mutations in the following description, any other methods which can detect specified mutant genes, such as the ASO method, the SSP method, direct sequencing can be used for the analysis. Primer sequences used in PCR can be any sequences which specifically amplify targeted gene regions and are not restricted to the sequences used in this Example.

At the time when this experiment was started, the following three kinds of mutations had been reported for this gene:

C478T mutation: cytosine at position 478 of exon 4 is substituted by thymine.
539AC deletion: adenine at position 539 and thymine at position 540 of exon 5 are deleted.
1159A insertion: adenine is inserted at position 1159 of exon 10.

The above-mentioned mutant genes can be identified by the PCR-RFLP method. The chromosomal DNAs used in the present experiment were identified by this method.

A method of detecting specified mutations used in the present invention will be explained as follows.

(1) Detection of Specified Mutations in Exon 4

(i) Preparation of Labeled Standard DNA

For exon 4, C478T mutation has been previously identified. A cleavage site for restriction enzyme Sau96I present in the wild-type gene is known to disappear by this mutation, thereby this mutant gene can be identified. A chromosomal DNA having the C478T mutant gene thus identified was amplified by PCR using unlabeled primers for CD36 exon 4 amplification, and the resultant amplification product was introduced into pT7Blue-T vector to transform *Escherichia coli*. A plasmid was prepared from the transformant thus obtained, and its base sequence was confirmed to obtain pEX04M.

Amplification by PCR was performed in a reaction solution (100 μl) using 10 pg each of pEX04W obtained in the previous section for detecting unspecified mutations in exon 4 and pEX04M obtained by the above-mentioned process as templates and 10 nmol each of labeled primers for CD36 exon 4 amplification to obtain wild-type and C478T mutant labeled standard DNAs. The reaction was carried out under the same conditions as described above.

(ii) Preparation of Unlabeled Sample DNA

A chromosomal DNA was prepared from peripheral blood lymphocytes of a patient using the above-mentioned kit. Using 50 ng of the chromosomal DNA as a template, PCR amplification was performed in a solution (50 μl) using 5 pmol each of unlabeled primers for CD36 exon 4 amplification and 1.5 units of Ampli Taq Gold.

(iii) Annealing by Temperature Gradient

A solution (final concentration 3.3×SSC, 30 μl) containing 1 μl of the labeled standard DNA and 15 μl of the unlabeled sample DNA was prepared. Annealing was carried out with temperature gradient after heat denaturation using the Gene Amp PCR System 96. That is, after heating at 98° C. for 10 minutes, the temperature was gradually lowered from 98° C. to 70° C. at a rate of 1° C./10 minutes.

To prepare a coloring positive control, heat denaturation and temperature-gradient annealing were performed with a solution prepared in the same manner as described above except that 15 μl of buffer solution for Ampli Taq Gold were added in place of the unlabeled sample DNA.

(iv) Coloring Reaction

Coloring was performed with the annealing solution (20 μl) prepared in (iii) using the system of ED-PCR. For each test sample, the ratio of the absorbance for the coloring positive control and the absorbance for the solution with the unlabeled sample DNA added was calculated, and the presence or absence of mutations was judged using the percentage of the reconstruction of the labeled DNA as an index.

(2) Detection of Specified Mutations in Exon 5

(i) Preparation of Labeled Standard DNA

For exon 5, a mutation with 539AC deletion has been previously identified. A chromosomal DNA having this mutant gene was amplified by PCR using unlabeled primers for CD36 exon 5 amplification, and the resultant amplification product was introduced into pT7Blue-T vector to transform *Escherichia coli*. A plasmid was prepared from the transformant thus obtained and its base sequence was confirmed to obtain pEX05M.

(ii) Preparation of Unlabeled Sample DNA

A chromosomal DNA was prepared from peripheral blood lymphocytes of a patient using the above-mentioned kit. Using 50 ng of the chromosomal DNA as a template, PCR amplification was performed in a solution (50 μl) using 5 pmol each of unlabeled primers for CD36 exon 5 amplification and 1.5 units of Ampli Taq God.

(iii) Annealing by Temperature Gradient

Annealing was carried out in the same manner as described for detecting specified mutations in exon 4.

(iv) Coloring Reaction

Coloring was performed in the same manner as described for detecting specified mutations in exon 4.

(3) Detection of Specified Mutations in Exon 10

(i) Preparation of Labeled Standard DNA

For exon 10, a mutation with 1159A insertion has been previously identified. A chromosomal DNA having this mutant gene was amplified by PCR using unlabeled primers for CD36 exon 10 amplification, and the resultant amplification product was introduced into pT7Blue-T vector to transform *Escherichia coli*. A plasmid was prepared from the transformant thus obtained, and its base sequence was confirmed to obtain pEX10M.

(ii) Preparation of Unlabeled Sample DNA

A chromosomal DNA was prepared from peripheral blood lymphocytes of a patient using the above-mentioned kit. Using 50 ng of the chromosomal DNA as a template, PCR amplification was performed in a solution (50 µl) using 5 pmol each of unlabeled primers for CD36 exon 10 amplification and 1.5 units of Ampli Taq God.

(iii) Annealing by Temperature Gradient

Annealing was carried out in the same manner as described for detecting specified mutations in exon 4.

(iv) Coloring Reaction

Coloring was performed in the same manner as described for detecting specified mutations in exon 4.

(1) Identification of Mutant Gene Ex13del12

Test sample #03 was suggested to have a mutation in exon 13 besides C478T mutation in exon 4 by the detection of specified and unspecified mutations in the CD36 gene. A method for the identification of the new mutant gene in exon 13 of the sample will be explained in detail as follows.

A solution for PCR containing the above-mentioned components was prepared using 100 ng of the chromosomal DNA of test sample #03 as a template, 100 pmol each of the unlabeled primers for CD36 exon 13 amplification (sequences described above) and 2.5 units of Ampli Taq Gold. PCR amplification was performed under the above-mentioned conditions. The resulting amplification product was subjected to 3% agarose gel electrophoresis to extract the targeted fragment. The fragment obtained was introduced into the pT7Blue-T vector to transform *Escherichia coli*. A plasmid DNA was prepared from the resultant transformant and the base sequence of the DNA was determination using ABI-PRISM377. As a result, it was revealed that the sample had deletion of 12 bases within exon 13. The protein produced from this mutant gene will have a deletion of 4 amino acids, namely Ile-Val-Pro-Ile.

Test samples #107, #201 and #326 were also revealed to have the same mutant genes.

(2) Identification of Mutant Gene Ex13dup43

Test sample #07 was suggested to have a mutation in exon 13 besides 539AC deletion in exon 5 by the detection of specified and unspecified mutations in the CD36 gene. The

TABLE 2

Results of the detection of specified mutations in exons 4, 5 and 10.

| | Exon #4 | | | Exon #5 | | | Exon #10 | | |
|---|---|---|---|---|---|---|---|---|---|
| | Index | | | Index | | | Index | | |
| | wild | mutant | Judgement | wild | mutant | Judgement | wild | mutant | Judgement |
| Sample | 100.0 | 100.0 | | 100.0 | 100.0 | | 100.0 | 100.0 | |
| Wild | 2.8 | 50.2 | wild | 5.1 | 59.5 | wild | 3.9 | 27.5 | wild |
| Hetero | 4.8 | 5.6 | hetero | 9.0 | 10.3 | hetero | 7.8 | 6.3 | hetero |
| mutant | 49.8 | 2.8 | mutant | 64.1 | 5.0 | mutant | 27.1 | 4.2 | mutant |
| #01 | 4.7 | 53.5 | wild | 10.2 | 68.1 | wild | 6.7 | 32.5 | wild |
| #101 | 6.0 | 8.9 | hetero | 9.3 | 61.4 | wild | 9.8 | 9.5 | hetero |
| #08 | 3.8 | 49.4 | wild | 17.1 | 16.1 | hetero | 6.3 | 35.0 | wild |
| #501 | 3.7 | 51.0 | wild | 8.5 | 64.0 | wild | 5.9 | 31.3 | wild |
| #502 | 5.9 | 8.1 | hetero | 8.2 | 61.1 | wild | 5.7 | 30.1 | wild |
| #503 | 3.8 | 49.5 | wild | 13.7 | 64.4 | wild | 5.3 | 32.3 | wild |
| #504 | 6.7 | 6.7 | hetero | 8.4 | 63.9 | wild | 5.3 | 31.8 | wild |
| #505 | 7.5 | 7.8 | hetero | 15.3 | 18.5 | hetero | 6.6 | 33.4 | wild |
| #506 | 3.9 | 51.4 | wild | 7.3 | 62.1 | wild | 5.4 | 33.4 | wild |
| #507 | 7.1 | 7.4 | hetero | 9.9 | 65.7 | wild | 5.7 | 32.5 | wild |

Wild: wild type. Hetero: mutations exist only in one allele. Homo: mutations exist on both alleles.

The following mutant genes were used.

Exon 4: C478T substitution. Exon 5: 539A insertion. Exon 10: 1159AC deletion.

In all the exons, indexes of less than 20 were judged to be positive.

Example 3
Identification of Novel Mutant Genes in the CD36 gene

Of the sequences of the CD36 gene of patients analyzed using the above-mentioned method and judged to have mutation in the section for unspecified mutations, the sequences for which no mutations were detected in the section for specified mutations are suggested to have novel mutant genes which have never been reported.

sample was amplified by PCR using the unlabeled primers for CD36 exon 13 amplification (sequences described above), then the base sequence was confirmed as described above. As a result, it was revealed that the sample had a duplication of 43 bp within exon 13. In consequence, a termination codon appears internally to stop the translation process, resulting in the production of an immature protein.

(3) Identification of Mutant Gene Ex13skip

Test sample #206 was suggested to have a mutation in exon 13 besides 1159A insertion in exon 10 by the detection of specified and unspecified mutations in the CD36 gene. The sample was amplified by PCR using the unlabeled primers for CD36 exon 13 amplification (sequences described above), then the base sequence was confirmed as described above. As a result, it was revealed that the sample had a deletion of 10 bases from an intron portion through an exon portion immediately before exon 13. In consequence, the sequence for the site of 3'-splice acceptor in the intron is expected to change, which results in abnormal splicing.

Determination of the cDNA sequence confirmed that in the sample, exon 12 was connected to exon 14, skipping exon 13 completely.

Further, the analysis showed that the intron sequence upstream of exon 13 of the wild-type CD36 gene be 5'-gttcataattattttcaacgta_ta_ttacg-exon13 and not 5'-gttcataattattttcaacgtattacg-exon 13 as previously reported in J. Biol. Chem., Vol. 22, 18985–18991 (1994).

(4) Identification of Mutant Gene T970C

Test sample #104 was suggested to have a mutation in exon 9 besides C478T mutation in exon 4 by the detection of specified and unspecified mutations in the CD36 gene. The sample was amplified by PCR using the unlabeled primers for CD36 exon 9 amplification (sequences described above), then the base sequence was confirmed as described above. As a result, it was confirmed that thymine at position 970 of exon 9 was substituted by cytosine. In consequence, Phe is substituted by Val in the protein expressed by this gene.

(5) Identification of Mutant Gene with 770A Insertion

Test sample #805 was suggested to have a mutation in exon 6 besides C478T mutation in exon 4 by the detection of specified and unspecified mutations in the CD36 gene. The sample was amplified by PCR using the unlabeled primers for CD36 exon 6 amplification (sequences described above), then the base sequence was confirmed as described above. As a result, it was confirmed that one base, thymine, was inserted at position 770 of exon 6. In consequence, reading frames are shifted and a termination codon is generated, which results in the expression of an immature protein.

(6) Identification of Mutant Gene T620C

Test sample #413 was suggested to have a mutation in exon 5 other than the previously reported mutation, i.e., 539AC deletion, by thedetectionof specified andunspecifiedmutations in the CD36 gene. The sample was amplified by PCR using the unlabeled primers for CD36 exon 5 amplification (sequences described above), then the base sequence was confirmed as described above. As a result, it was confirmed that thymine at position 620 of exon 5 was substituted by cytosine. In consequence, Val is substituted by Ala in the protein expressed by this gene.

The results of the analysis for the test sample #413 are shown as follows. Table 3 shows results of the detection of unspecified mutations. Table 4 shows results of the detection of the specified mutation, 539ACdel, previously known for exon 5.

TABLE 3

Results of the detection of unspecified mutation in exon 5 for multiple test samples including test sample #413

| Subject | Sample | A405 (nm) Wild | Index | Judge |
|---|---|---|---|---|
| #401 | 1.770 | 0.075 | 4.2 | Wild |
| #402 | 1.593 | 0.054 | 3.4 | Wild |
| #403 | 1.937 | 0.088 | 4.5 | Wild |
| #404 | 1.577 | 0.054 | 3.4 | Wild |
| #405 | 2.072 | 0.091 | 4.4 | Wild |
| #406 | 2.072 | 0.101 | 4.9 | Wild |
| #407 | 1.805 | 0.083 | 4.6 | Wild |
| #408 | 1.936 | 0.079 | 4.1 | Wild |
| #409 | 2.420 | 0.183 | 7.6 | wild |

TABLE 3-continued

Results of the detection of unspecified mutation in exon 5 for multiple test samples including test sample #413

| Subject | Sample | A405 (nm) Wild | Index | Judge |
|---|---|---|---|---|
| #410 | 2.289 | 0.150 | 6.6 | wild |
| #411 | 2.348 | 0.130 | 5.5 | wild |
| #412 | 2.359 | 0.150 | 6.4 | wild |
| #413 | 2.039 | 0.475 | 23.3 | hetero |

TABLE 4

Detection of the specified mutation in exon 5 for test sample #413

| | Wild-type | | 539ACdel | |
|---|---|---|---|---|
| | A405 | Index | A405 | Index |
| #404 | 0.180 | 10.8 | 1.520 | 91.8 |
| #406 | 0.163 | 9.8 | 1.487 | 89.9 |
| #407 | 0.120 | 7.2 | 1.533 | 92.6 |
| #413 | 0.276 | 16.6 | 1.616 | 97.6 |
| Sample | 1.665 | | 1.655 | |

Cutoff values smaller than 20 were judged to be positive. The results in Table 3 conclude that test sample #413 has a certain mutation in exon 5, but it has no 539ACdel mutant gene as previously reported. Accordingly, it was strongly suggested that the sample had a novel mutant gene.

(7) Identification of Mutant Gene T716G

Test sample #872 was suggested to have a mutation in exon 6 other than 770A insertion (770insA), which was revealed by the present invention, by the detection of specified and unspecified mutations in the CD36 gene. The sample was amplified by PCR using the unlabeled primers for CD36 exon 6 amplification (sequences described above), then the base sequence was confirmed as described above. As a result, it was confirmed that thymine at position 716 of exon 6 was substituted by guanine. In consequence, this gene produces a protein in which the amino acid at position 169, originally methionine (ATG), is mutated to arginine (ACG). (8) Identification of mutant gene Ex12Skip Test sample #811 was suggested to have a mutation in exon 12 besides C478T mutation in exon 4 by the detection of specified and unspecified mutations in the CD36 gene. The sample was amplified by PCR using the unlabeled primers for CD36 exon 12 amplification (sequences described above), then the base sequence was confirmed as described above. As a result, it was revealed that 7 bases were deleted at an intron portion present upstream of exon 12. In consequence, the sequence for the site of 3'-splice acceptor in the intron is expected to change, which results in abnormal splicing. Determination of the cDNA sequence confirmed that in the sample, exon 11 was connected to exon 13, skipping exon 12 completely.

What is claimed is:

1. A CD36 mutant gene comprising a nucleotide sequence selected from the sequences of SEQ ID NO: 1 through SEQ ID NO: 8.

2. A CD36 mutant gene according to claim 1, which is selected from the sequences consisting of:
 a CD36 mutant gene sequence of the CD36 gene sequence (SEQ ID NO: 38) in which the mutated portion of SEQ ID NO: 38 is the nucleotide sequence of SEQ ID NO: 1, 2 or 3;
 a CD36 mutant gene sequence of the CD36 gene sequence (SEQ ID NO: 39) in which the mutated portion of SEQ ID NO: 39 is the nucleotide sequence of SEQ ID NO: 4;
 a CD36 mutant gene sequence of the CD36 gene sequence (SEQ ID NO: 41) in which the mutated portion of SEQ ID NO: 41 is the nucleotide sequence of SEQ ID NO: 5;
 a CD36 mutant gene sequence of the CD36 gene sequence (SEQ ID NO: 42) in which the portion of SEQ ID NO: 42 is the nucleotide sequence of SEQ ID NO: 6 or 7; and
 a CD36 mutant gene sequence of the CD36 gene sequence (SEQ ID NO: 43) in which the mutated portion of SEQ ID NO: 43 is the nucleotide sequence of SEQ ID NO: 8.

3. A nucleotide sequence fragment comprising a nucleotide sequence selected from the sequences of SEQ ID NO:1 through SEQ ID NO:8, or a mutated portion thereof.

4. A nucleotide sequence fragment according to claim 3, wherein the mutated portion is a nucleotide fragment consisting of at least 12 consecutive nucleotides of a nucleotide sequence selected from SEQ ID NO:1 through SEQ ID NO:8, and the consecutive nucleotides have a mutation.

5. A nucleotide sequence fragment according to claim 3 or 4 which is a probe for detecting a mutation of the CD36 gene.

6. A primer which detects a mutation of the CD 36 gene comprising a nucleotide fragment consisting of at least 12 consecutive nucleotides of the CD36 mutant gene nucleotide sequence or a full complement thereof.

7. A primer pair consisting of two primers according to claim 6.

8. A nucleotide sequence fragment obtained by amplifying a CD36 mutant gene with the primer pair according to claim 7.

9. A method for diagnosing a disease caused by abnormal lipid metabolism, comprising a step of detecting a mutation of the CD36 gene wherein the step of detecting the mutation of the CD36 gene comprises the steps of hybridizing the nucleotide fragment according to claim 3 with a nucleic acid sample isolated from a subject and then detecting the presence of a hybridization complex which indicates the presence of a mutation in the CD36 gene.

10. A method according to claim 9 wherein the mutation of the CD36 gene is a mutation given in exon 4, exon 5, exon 6, exon 9, exon 10, exon 12, or exon 13.

11. A method according to claim 9 wherein the mutation of the CD36 gene is a mutation given in SEQ ID NO: 1 through SEQ ID NO: 8.

12. A method according to claim 9 wherein the disease caused by lipid metabolism abnormality is a disease selected from the group consisting of cardiomyopathy, juvenile sudden death, and accidents in surgical operations.

13. A method according to claim 9 wherein the step of detecting the mutation of the CD36 gene further comprises the steps of amplifying a nucleic acid sample isolated from a subject and a standard nucleic acid sample with the primer pair according to claim 7, subjecting the resulting amplified products to the conditions of the substitution of the complementary strands, and detecting the degree of the substitution of the complementary strands which indicates the presence of a mutation in the CD36 gene.

14. A kit for the diagnosis of a disease caused by abnormal lipid metabolism, comprising a reagent for detecting a mutation of the CD36 gene wherein the reagent for detecting the mutation comprises a nucleide fragment consisting of at least 12 consecutive nucleotides of the CD36 mutant gene according to claim 1 or a full complement thereof.

* * * * *

UNITED STATES PATENT AND TRADEMARK OFFICE
CERTIFICATE OF CORRECTION

PATENT NO. : 6,306,603 B1
DATED : October 23, 2001
INVENTOR(S) : Oka et al.

It is certified that error appears in the above-identified patent and that said Letters Patent is hereby corrected as shown below:

<u>Tilte page,</u>
Item [73], the Assignee's information should read:

-- [73] Assignee: Wakunaga Pharmaceutical Co., Ltd., Osaka-shi, (JP) --

Signed and Sealed this

Eighteenth Day of June, 2002

*Attest:*

*Attesting Officer*

JAMES E. ROGAN
*Director of the United States Patent and Trademark Office*